(12) United States Patent
Faulhaber et al.

(10) Patent No.: US 10,307,531 B2
(45) Date of Patent: Jun. 4, 2019

(54) APPARATUS FOR RECEIVING A SYRINGE IN A FLUID-DISPENSING APPARATUS AND A METHOD FOR SAME AND USE OF SUCH A RECEPTACLE

(71) Applicant: Fresenius Medical Care Deutschland GmbH, Bad Homburg (DE)

(72) Inventors: Thomas Faulhaber, Bergrheinfeld (DE); Thomas Weingaertner, Gerbrunn (DE)

(73) Assignee: FRESENIUS MEDICAL CARE DEUTSCHLAND GMBH, Bad Homburg (DE)

(*) Notice: Subject to any disclaimer, the term of this patent is extended or adjusted under 35 U.S.C. 154(b) by 603 days.

(21) Appl. No.: 14/768,344

(22) PCT Filed: Mar. 19, 2014

(86) PCT No.: PCT/EP2014/055550
§ 371 (c)(1),
(2) Date: Aug. 17, 2015

(87) PCT Pub. No.: WO2014/147150
PCT Pub. Date: Sep. 25, 2014

(65) Prior Publication Data
US 2016/0000996 A1    Jan. 7, 2016

(30) Foreign Application Priority Data

Mar. 21, 2013    (DE) ................. 10 2013 004 860

(51) Int. Cl.
*A61M 5/145*    (2006.01)
*A61M 5/50*    (2006.01)

(52) U.S. Cl.
CPC ........ *A61M 5/1458* (2013.01); *A61M 5/5086* (2013.01); *A61M 5/1452* (2013.01);
(Continued)

(58) Field of Classification Search
CPC ...... A61M 5/1458; A61M 2005/14506; A61M 5/1452; A61M 5/14546; A61M 5/31; A61M 5/31576
See application file for complete search history.

(56) References Cited

U.S. PATENT DOCUMENTS 4,137,940 A * 2/1979 Faisandier .......... A61M 5/1689
137/486
5,545,140 A * 8/1996 Conero ............... A61M 5/1456
128/DIG. 1

(Continued)

FOREIGN PATENT DOCUMENTS

EP    0514907    11/1992
EP    0916353    5/1999
(Continued)

*Primary Examiner* — Bradley J Osinski
*Assistant Examiner* — Nilay J Shah
(74) *Attorney, Agent, or Firm* — Jacobson Holman, PLLC.

(57) ABSTRACT

A device for receiving, without play, a syringe in a fluid-dispensing apparatus has at least two elastically prestressable clamps that grip the flange of the syringe plunger, and an elongated hole is provided for each clamp, such that during operation the clamp grips the plunger flange and slides in the elongated hole while simultaneously moving in a rotational and translatory manner.

17 Claims, 7 Drawing Sheets

(52) U.S. Cl.
CPC .................. *A61M 5/14546* (2013.01); *A61M 2005/14506* (2013.01)

(56) References Cited

U.S. PATENT DOCUMENTS

| | | | |
|---|---|---|---|
| 6,428,509 B1 * | 8/2002 | Fielder | A61M 5/1456 604/131 |
| 8,070,732 B2 | 12/2011 | Rochette | |
| 2004/0039344 A1 | 2/2004 | Baldwin et al. | |
| 2008/0154200 A1 * | 6/2008 | Lesch | A61M 5/2033 604/135 |
| 2011/0178359 A1 | 7/2011 | Hirschman et al. | |
| 2012/0195793 A1 | 8/2012 | Oesterreich et al. | |

FOREIGN PATENT DOCUMENTS

| | | |
|---|---|---|
| EP | 1005875 | 6/2000 |
| EP | 1200143 | 5/2002 |
| EP | 1588729 | 10/2005 |
| EP | 1847285 | 10/2007 |
| JP | S63-102766 | 5/1988 |
| JP | H09122238 | 5/1997 |
| JP | 2003520625 | 7/2003 |
| JP | 2004236734 | 8/2004 |
| JP | 2005052367 | 3/2005 |
| JP | 2005287944 | 10/2005 |
| JP | 2010525868 | 7/2010 |
| WO | WO 01/08726 | 2/2001 |

\* cited by examiner

APPARATUS FOR RECEIVING A SYRINGE IN A FLUID-DISPENSING APPARATUS AND A METHOD FOR SAME AND USE OF SUCH A RECEPTACLE

The invention relates to an apparatus for receiving a syringe in a fluid-dispensing apparatus and a method for doing so. The invention also relates to a treatment unit having an apparatus according to the preamble of claim 1. In addition, the invention relates to the use of an apparatus for receiving a syringe in a fluid-dispensing apparatus. This apparatus may be used in many fields, e.g., in the industrial, analytical, pharmaceutical or medical fields.

It is known that dosing mechanisms in the form of so-called dosing pumps are to be used to deliver precisely metered quantities of fluid. These dosing pumps deliver a defined volume per stroke and per unit of time, regardless of the pressure conditions at the inlet and outlet of the pump.

Dosing pumps are used in medicine in particular because precise dosing of medications and maintaining a constant active ingredient concentration are especially important in this field.

The dosing pumps used in medicine for dosing pharmaceutical drugs in continuous intravenous administration are known as infusion pumps.

So-called syringe pumps are also used in medicine. This type of pump is understood to be a dosing pump for intravenous administration of medicine, which is contained in syringes that are inserted into the receptacle provided for this purpose in the infusion pump.

In special cases, the syringe pump may be a heparin pump, which is used together with a dialysis machine for accurate dosing of drugs (anticoagulants), which help to inhibit the coagulation of blood.

A syringe consists of a cylindrical cavity the syringe sleeve, in which a movable plunger can slide up and down. The syringe sleeve is sealed at the distal end by a cover plate, which ends in a cone that is open distally, in the syringe nozzle or in a thread, for example, a Luer Lock. A hollow needle or a tube may be connected to the cone and/or the Luer Lock. There is usually a plunger stop on the proximal end of the syringe sleeve to prevent the syringe plunger from slipping out.

Conventional disposable syringes are made of plastic, while reusable syringes, which are not used as often today, may be manufactured from glass, metal or rubber.

As is known in general, syringes from various manufacturers are available in different sizes. Conventional commercial syringes usually reach a volume of 0.5 mL to 100 mL.

Even if syringes are designed to hold the same quantities of fluid, there may be substantial differences from one manufacturer to the next in the external, dimensions of the syringe in both length and diameter.

Not only are the diameter and length of the syringe sleeve highly variable, but also the plunger lengths and their diameters, and in particular the plunger flange may vary in thickness. With commercial syringes, the thickness of the plunger flange is between 1.2 mm and 3.0 mm, for example, To empty the syringe inserted into an syringe pump, a drive element moves the plunger in a linear movement in the syringe. The plunger flange is therefore surrounded by a holder, which is connected to the drive element. It is important to ensure that the plungers of syringes of different sizes are held tightly and securely.

Numerous fluid-dispensing systems which contain different devices to receive and hold syringes are already known from the prior art.

For example, the document E 1 847 285 describes a fluid injection system having a gripping mechanism comprised of a pair of clamping hooks which can be opened and closed individually at the side to detect a right edge and a left edge of the plunger flange. Sensors and an evaluation unit can reveal whether the clamping hooks have first opened and then closed again.

E 0 514 907 describes a device for driving the plunger of syringes of different sizes. It has a pair of curved arms which are preloaded to one another by means of a spring force and exert a force in the direction of the center of the plunger flange. Another clamp serves to hold the syringe in the receptacle.

EP 1 200 143 is also concerned with a drive system for fluid-dispensing apparatuses which can receive different syringe sizes. Two pivotable spring-loaded arms hold the flange of the immersion plunger of the syringe from its inside out pressed against the pressure surface of the drive system while at the same time gripping and clamping the shaft of the plunger. This should prevent the syringe plunger from moving into the syringe based on a so-called "siphon effect," i.e., a suction into the syringe, and thus inadvertently dispensing fluid out of the syringe.

EP 1 005 875 describes a fluid infusion apparatus having a holding mechanism which also retains the flange of the syringe plunger mechanically to prevent a negative pressure on the syringe arranged in the fluid infusion apparatus from pulling the plunger into the syringe. The document cited here is a further development of the document. EP 0 916 353.

European Patent EP 1 588 729 proposes a system for dispensing fluid, which has two rotating clamping hooks with bent ends. A spring connecting the two hooks to one another automatically closes the hook after inserting a syringe, so that the flange of the plunder is gripped by a rotational movement of the clamping hooks.

U.S. Pat. No. 8,070,732 describes an infusion pump having a holder whose two gripping arms that are movable via gearwheels are moved by translatory and rotatory movements in succession to grip the plunger flange. The gripper arms are connected to one another via gearwheels.

To be able to receive syringes regardless of their size, a relatively great "play" is defined in the design of the syringe receptacle in most cases.

The term "play" refers to the freedom of movement, which is determined by the production and the application, so that a mechanical subassembly can move freely with or against another component after mounting. In the normal case, a great play is advantageous with regard to problem-free mounting, preventing stresses, insensitivity to temperature fluctuations and soiling, for example.

However, in the use of syringe pumps with an excessively great play, there is the risk of faulty dosing of the medication. In dosing in the reduced pressure range in particular, there may be a change in the contact surface between the plunger receptacle and the syringe plunger. With each change, the play is forced out, which is then manifested as a minor dosing error.

A negligibly small play between the parts and in particular a connection of the injection plunger to the drive mechanism without any play in the sense of a press fit are advantageous here.

The patent applications cited are concerned with the problem of accommodating different syringe sizes. However, they do not disclose how a syringe receptacle can be free of play.

The object of the present invention is therefore to make available a device and a method which will make it possible to accommodate the syringe plunger independently of the size of the syringe and to hold it in this position securely and thus eliminate the disadvantages of the previous systems.

Another object of the present, invention is the ease of use, i.e., convenient and easy insertion of the syringe.

In addition, the device should be simple and inexpensive to manufacture.

This object is achieved according to the invention by the features of the device (apparatus) and method described below. The device has at least two resiliently prestressable clamping means to receive the syringe in a fluid-dispensing apparatus, these clamping means gripping the plunger flange of a syringe plunger, such that an elongated hole is provided for each clamping means, so that the clamping means slides in this elongated hole and thus executes both rotational and translatory movements at the same time during the gripping operation.

Advantageous embodiments of the invention, are derived from the following description.

The invention includes a technical medical treatment unit with the apparatus according to the invention.

The invention includes use of the apparatus according to the invention for administering a fluid, which is suitable for use in the industrial field, preferably in the analytical, medical and pharmaceutical fields.

The invention includes and evaluation unit for the apparatus according to the invention, having sensors which indicate the position of the plunger flange and of the holding element.

The apparatus according to the invention consists of a holder, at least two clamping means and a housing in which the clamping means are secured.

The housing may consist of an upper half and a lower half.

The holder is part of a dosing device, which is an infusion pump in a preferred embodiment and is connected to a drive mechanism.

In a special embodiment, the dosing device is an integral component of a device plate oils detachably connectable thereto via fastening mechanisms. The device plate may be part of a medical treatment device in certain embodiments.

The drive mechanism is capable of moving the plunger of a syringe to empty the fluid in it.

A syringe consists of a cylindrical cavity, the syringe sleeve, which has different lengths and thicknesses and in which a movable plunger of a suitable size can move up and down axially to the syringe.

The fluid is generally understood to include liquids, gases, emulsions or suspensions. In certain embodiments, the fluid may be a medical fluid, for example, blood, dialysate, substitute, a rinsing solution, priming solution, sterilization solution or medication solution and the like. In one special embodiment, the fluid is a medication solution.

To empty the syringe, which has been inserted into an syringe pump, a drive mechanism pushes the plunger of the syringe in a line toward it. To do so, the plunger flange is connected to the drive mechanism via the holder via suitable clamping means.

The drive mechanism is based on an electric motor but also a mechanical spring operation and/or pneumatic operation and/or magnetic, operation is also conceivable.

The clamping means consist of an operating element and a holding element. The two elements may also be connected to one another in one piece.

The operating element is operated by the user to separate the holding element, which holds the plunger flange, from the syringe plunger. A cross brace by which the clamping means are held in the housing is located at the transition from the actuating element to the holding element.

Two spacer wheels on the two ends of the cross braces ensure a sufficiently great distance between the actuating element and/or the holding element and the housing to permit frictionless movement.

Two protrusions are formed on the cross brace, the "first" having a hook-like shape and the "second" having a curve-like shape.

The hook-like protrusion is connected to a pressure plate by means of which a prestress of the clamping means can be built up by means of at least one spring.

The prestressed spring at least cancels the force of the reduced pressure, which occurs in the syringe during operation and thus prevents the plunger from being retracted into the syringe due to the vacuum with the resulting unintentional dispensing of liquid.

The minimum spring force (Fmin) and the maximum spring force (Fmax) required for this correlate with the thickness of the plunger flange.

To determine the spring force Fmin and Fmax, a ratio is formed between the vacuum in the syringe (pmin, pmax) and the spring tension (Fnenn). The spring tension is a function of the design of the spring, i.e., its length, material and winding.

The force required for actuation of the clamping means is obtained from the ratio of the different variables, i.e., the design of the spring, the thickness of the plunger flange and the spring force.

On actuation of the clamping means, the curve-like protrusion slides out of a recess onto an elevation.

The angle of the elevation may preferably be between 0° and 50°. If the angle is greater, the force required for actuation of the clamping means is increased.

If the spring force and angle of the elevation are coordinated with one another suitably, then the clamping means can be operated by the user with one hand. Convenient insertion or removal of the syringe is thus possible.

In actuation of the clamping means, the cross brace is rotated about its own axis on the one hand and on the other hand performs the sliding out of the recess and sliding onto the elevation in the longitudinal hole provided for this purpose axially to the plunger of the syringe, so that a translatory movement and a rotational movement take place at the same time.

Due to the linkage of these two forms of movement, the holding element grips the plunger flange at the sides, inserting it from above and thus ensuring a play-free hold even with variable plunger flange thicknesses from 1.2 mm to 3.00 mm, in contrast with a strictly curved movement.

The holding element also ensures a tight and secure hold of the syringe plunger in a precise position for the duration of the administration.

In a special embodiment, an evaluation unit having at least one sensor by means of which information about the position of the syringe plunger and/or the holding element can be obtained is integrated into the housing. By determining the position of the syringe plunger, play-free contact of the plunger flange with the housing can be determined and by means of the position of the holding element, its degree of opening can also be determined.

All the elements of the apparatus for receiving a syringe are made of a material that has dimensional stability and a low wear. In certain embodiments, the material may be a thermoplastic or a metal, for example.

Use of a freely obtainable material and the reduction to a few parts permit an inexpensive and simple production and ensure that only a few parts are subject to possible wear or a defect. Thus the maintenance expense for the entire system can be reduced.

The apparatus for receiving a syringe can be thought of in certain embodiments as a disposable item, which is discarded after use, for example, together with the syringe.

The device described here can be used in many areas such as in the industrial, analytical, pharmaceutical and medical fields.

The invention is explained in greater detail below with reference to the drawings.

In these drawings.

Figure 1:
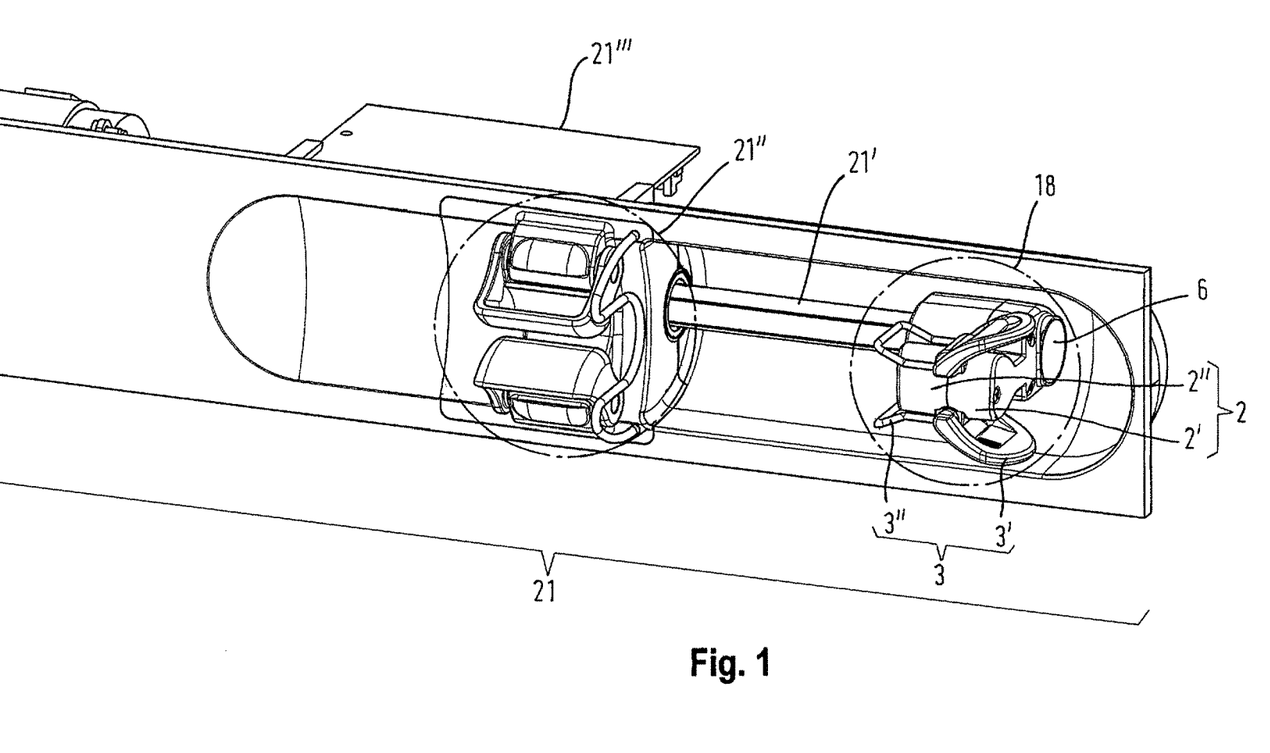
FIG. 1 shows a three-dimensional diagram of a fluid-dispensing apparatus having a receiving apparatus according to the invention.

FIG. 1 shows a fluid-dispensing apparatus 21 with the receiving apparatus 18 according to the invention in a three-dimensional diagram, said apparatus optionally being made of a material having dimensional stability, preferably plastic or metal. The receiving apparatus 18 is connected to a sliding rod 21 via an opening 5. The sliding rod can be moved by means of a drive mechanism. The syringe sleeve is inserted into the syringe holder 21". The fluid-dispensing apparatus 21 may be connected to a medical technical apparatus via a fastening mechanism 21'''.

Figure 2:
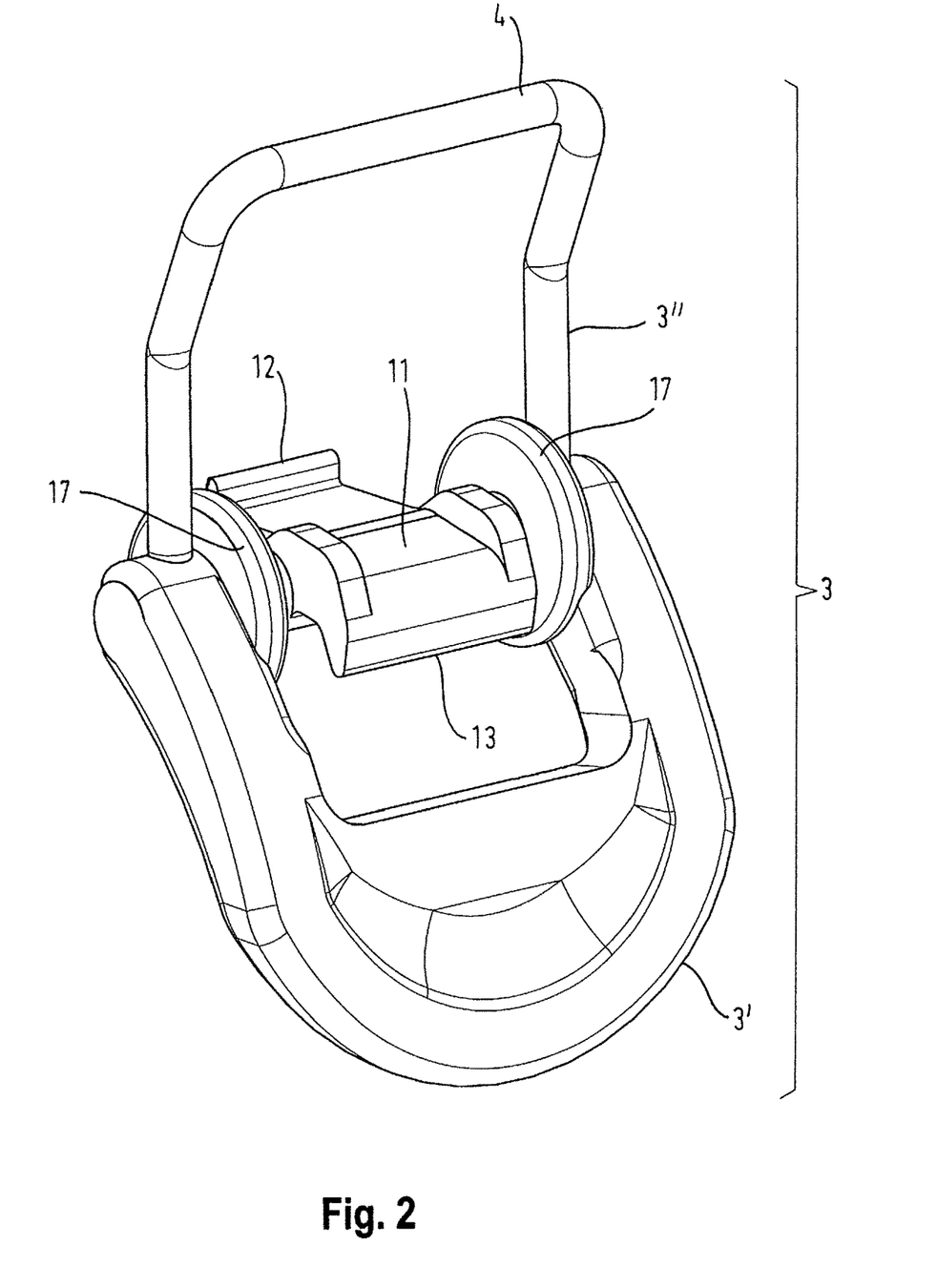
FIG. 2 shows a three-dimensional diagram of the clamping means.

FIG. 2 shows a schematic three-dimensional diagram of the clamping means 3. The actuating element 3 and the holding element 3" are connected by means of a cross brace on which there is also a hook-like protrusion 12 and a curve-like protrusion 13. The hook-like protrusion 12 of the cross brace 11 is connected to a pressure plate 8, by means of which the clamping means 3 can be prestressed by means of at least one spring 7. The curve-like protrusion 13 on the cross brace 11 lies in a recess 14 in its starting position, i.e., when the clamp is open. The actuating element and retaining element may also be designed in one piece.

Figure 3:
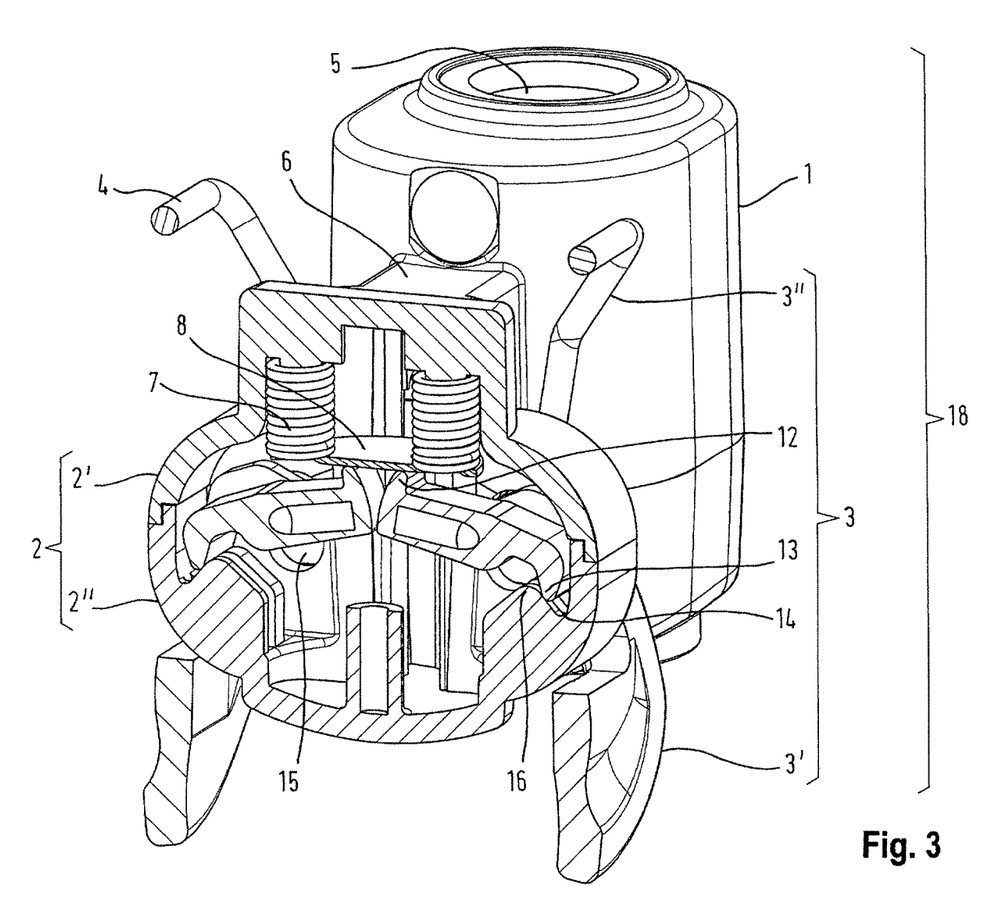
FIG. 3 shows a three-dimensional diagram of an embodiment of the apparatus according to the invention with the clamping means opened and with the housing in a longitudinal section.

FIG. 3 shows one embodiment of the apparatus according to the invention in a three-dimensional diagram with the clamping means 3 opened and with the housing 2 shown in a longitudinal sectional view.

The receiving apparatus 18 according to the invention has a housing 2, which is attached to a holder 11 provided with an opening 5 for a sliding rod. The housing consists of an upper half 2' and a lower half 2" A one-piece design of the housing 2 is also conceivable.

Two clamping means 3 are held in an elongated hole 15 in the housing 2 by means of one cross brace 11 each.

The clamping means 3 in turn consist of an actuating element 3' and a holding element 3". The holding element has a clamp-like end 4 and thus grips the plunger flange. The thickness of the plunger flange may be 1.2 mm to 3.0 mm. The cross brace 11 is situated at the transition between the actuating element 3' and the holding element 3" and in turn has a spacer wheel 17 at each end. The spacer wheel 17 ensures a sufficiently great distance from the housing 2 in order to permit movement without friction.

In one embodiment, the receiving apparatus is an integral component of a medical technical treatment unit or is detachably connected to such a unit, via a fastening mechanism 21''' and serves to administer a fluid.

The receiving apparatus may also preferably be integrated into a fluid-dispensing apparatus, preferably a dosing device in particular an infusion pump and especially a syringe pump or may be detachably connected to same.

In a particularly preferred embodiment, the receiving apparatus is an integral component of a heparin pump or is detachably connected to same.

Figure 4:
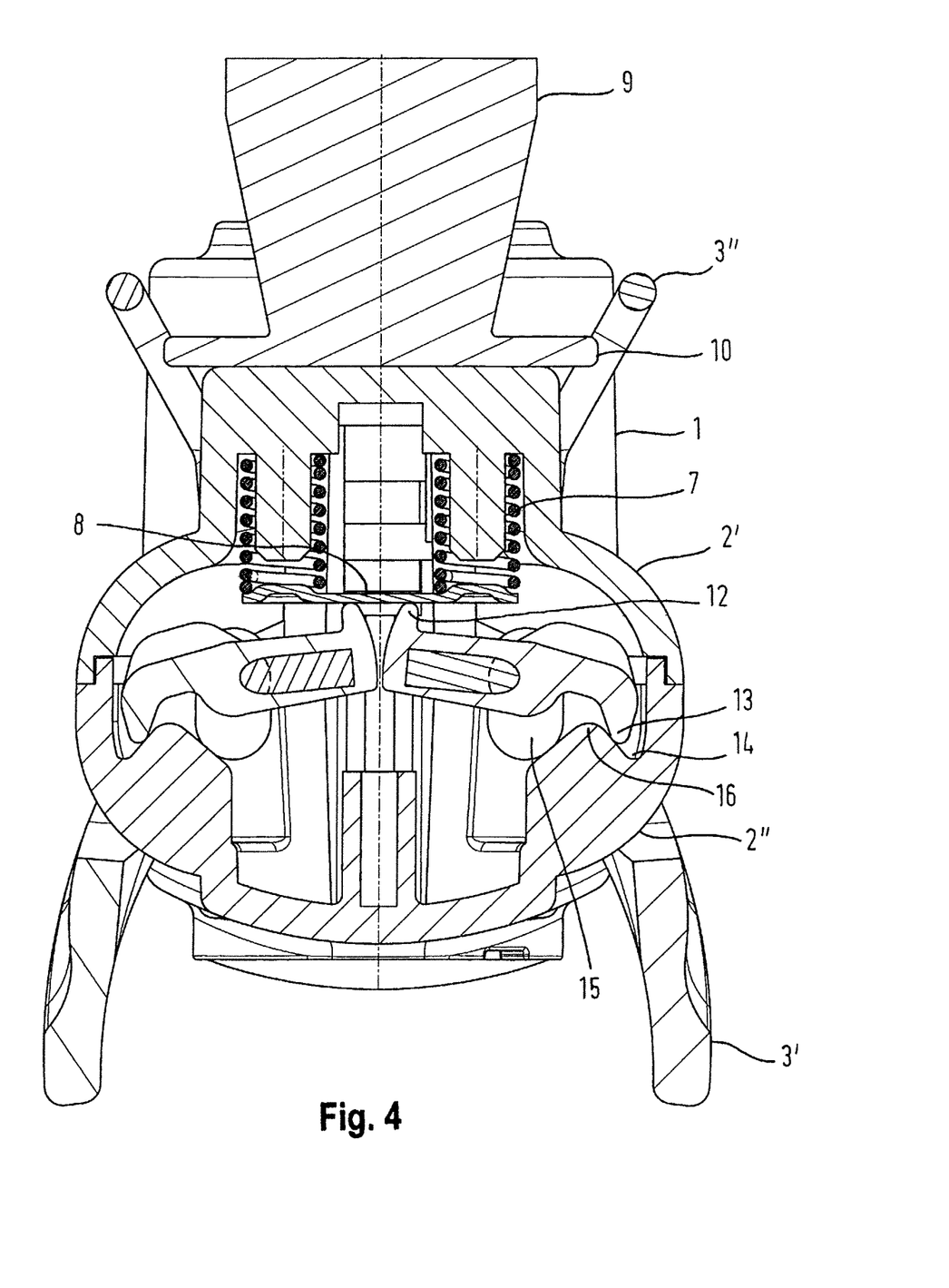
FIG. 4 shows a schematic diagram of one embodiment of the apparatus according to the invention with the clamping means opened in a longitudinal section.

FIG. 4 shows in a schematic diagram one embodiment of the receiving apparatus 1 according to the invention with opened clamping means in a longitudinal section.

Figure 5:
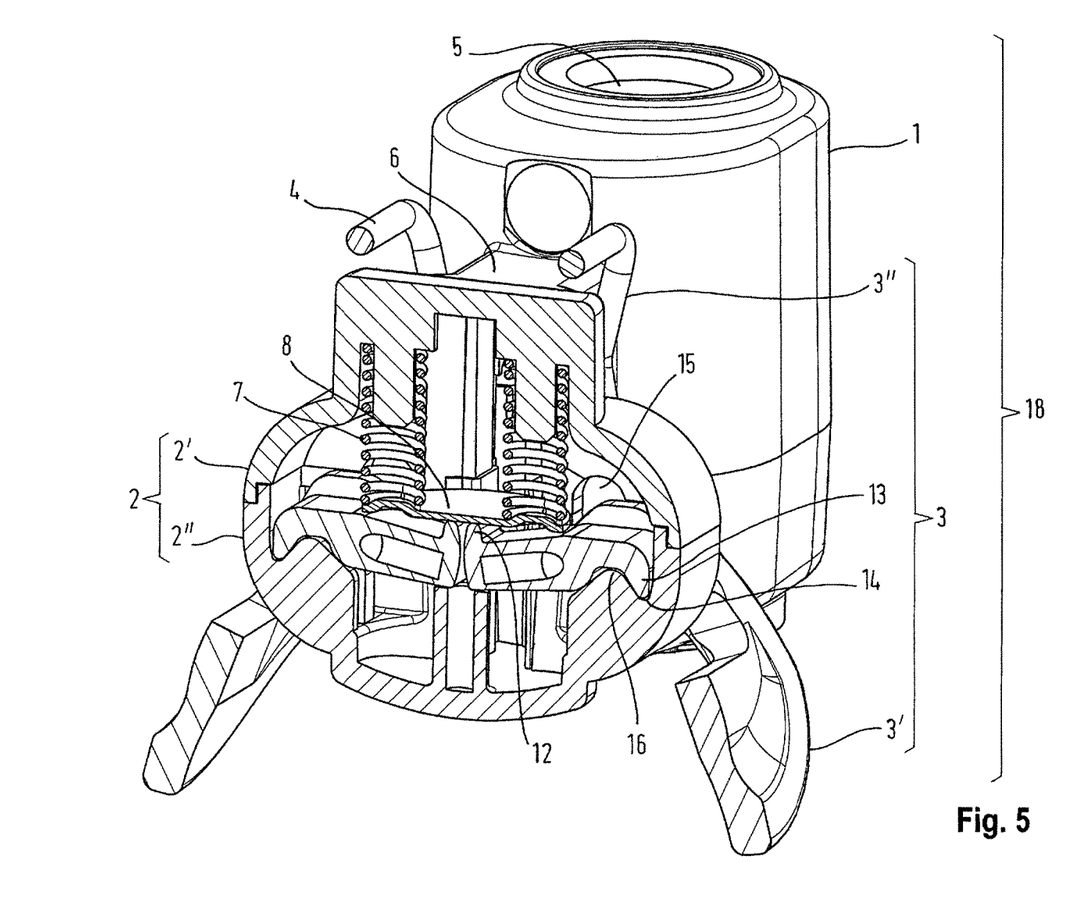
FIG. 5 shows a three-dimensional diagram of one embodiment of the apparatus according to the invention with the clamping means closed and with the housing in a longitudinal section.

FIG. 5 shows one embodiment of the apparatus according to the invention in a three-dimensional diagram with the clamping means 3 closed in a housing 2 shown in a longitudinal section.

For inserting the syringe plunger 9 into the receiving apparatus 18, the actuating element 3' of the clamping means 3 must be activated.

The curve-like protrusion 13 then slides out of the recess onto the elevation 16. The cross brace 11 therefore moves upward in the direction of the syringe plunger 9 (translatory movement) in the direction axial to the syringe in the elongated hole 15 and at the same time rotates about its own axis (rotational movement). The angle of the elevation may preferably be between 0° and 50°. The hook-like protrusion 12 on the cross brace 11 moves the pressure plate 8 upward in the direction of the syringe plunger and compresses the spring 7. The holding element 3" is now spread apart.

If the syringe plunger 9 is in its intended position, the actuating element 3 of the clamping means 3 is released.

The spring 7 relaxes and forces the pressure plate 8 downward onto the hook-like protrusion 12. The cross brace 11 therefore rotates back and at the same time moves downward in the longitudinal hole 15 axially to the syringe, i.e., moving away from the syringe plunger 9. The curve-like protrusion 13 slides back from the elevation 16 into the recess 14.

Due to these simultaneous translatory and rotational movements, the holding element grips the plunger flange from the side and inserts it from above. The clamp-like end 4 of the holding element 3" comes to lie on the inner side of the plunger flange 10.

Thus a play-free tight, secure and accurately positioned holding of the syringe plunger is ensured even with varying plunger flange thicknesses from 1.2 mm to 3.00 mm.

To separate the holding element 3" from the plunger flange 10 again, the actuating element is operated again. This permits convenient withdrawal of the syringe.

A suitable combination of prestress of the spring and a cam curvature permits one-ended operation of the receiving apparatus.

Figure 6:
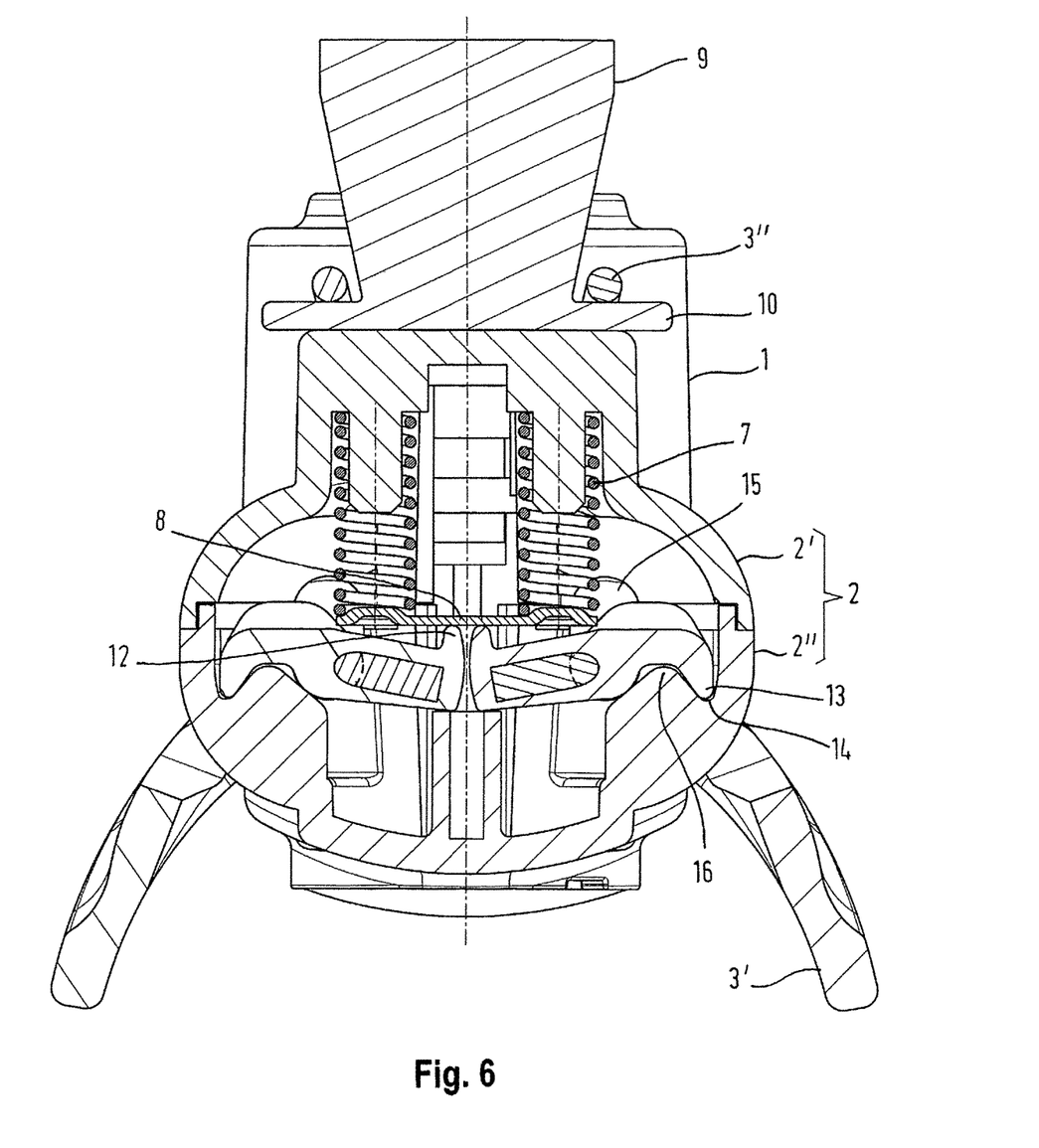
FIG. 6 shows a schematic diagram of one embodiment of the apparatus according to the invention with the clamping means opened in a longitudinal section.

FIG. 6 shows a schematic diagram of an embodiment of the receiving apparatus 1 according to the invention with the clamping means closed, shown in a longitudinal section.

Figure 7:
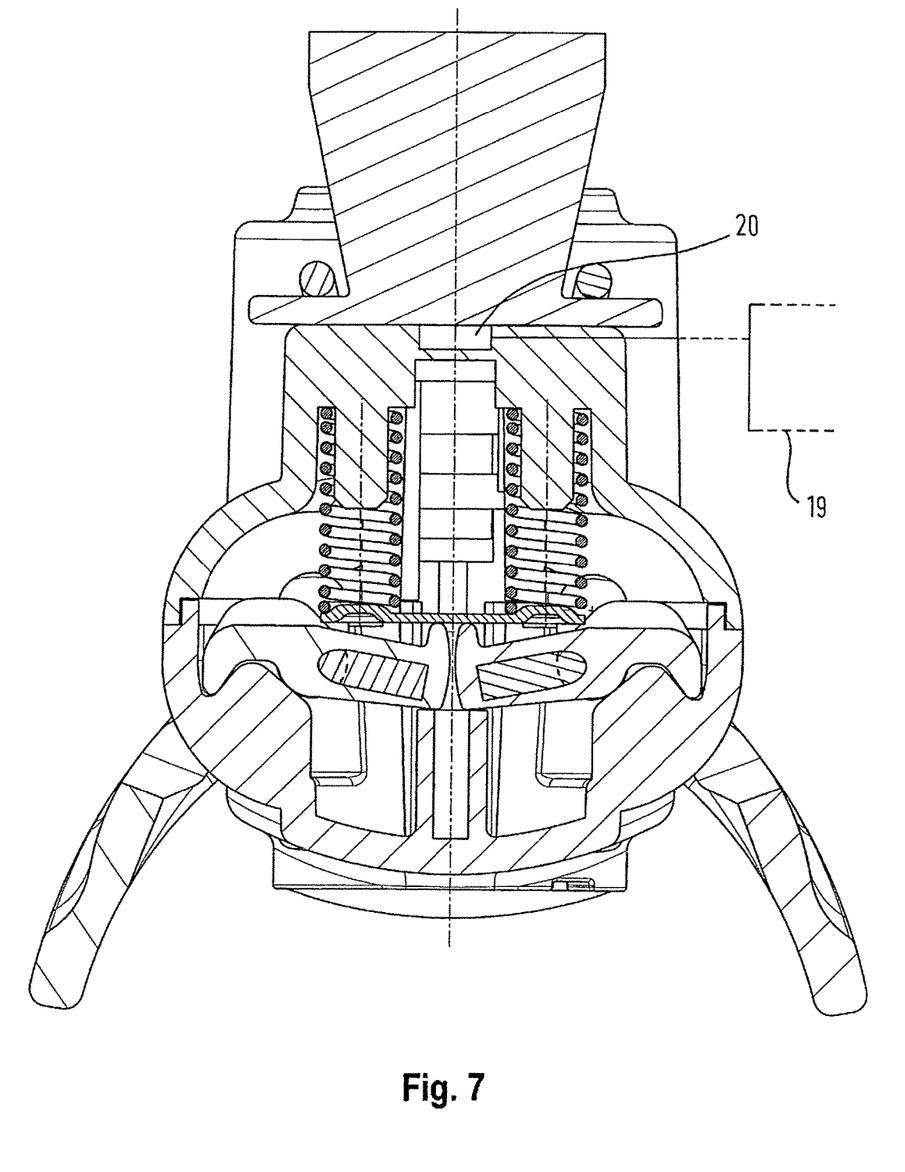
FIG. 7 shows a three-dimensional diagram of the clamping means

FIG. 7 shows a schematic diagram of one embodiment of the receiving apparatus 1 according to the invention with the clamping means closed, shown in a longitudinal section with an evaluation unit 19 connected to at least one sensor 20. The sensor 20 is preferably in the upper part of the housing 2 and allows inferences regarding the position of the plunger flange 9 and the holding elements 3''. If the syringe is not properly inserted, i.e., if the plunger flange 9 is not in flat contact with the receiving surface 2''' of the housing 2 or if the holding elements have not opened or closed properly, then an alarm signal is produced or the operation of the dosing device is stopped.

| | |
|---|---|
| 1 | holder |
| 2 | housing |
| 2' | top part of the housing |
| 2'' | bottom part of the housing |
| 3 | clamping means |
| 3' | actuating element of the clamping means |
| 3'' | holding element of the clamping means |
| 4 | clamp-like end of the holding element |
| 5 | opening for a sliding rod |
| 6 | plunger flange support |
| 7 | spring |
| 8 | pressure plate |
| 9 | syringe plunger |
| 10 | plunger flange |
| 11 | cross brace |
| 12 | hook-like protrusion |
| 13 | curve-like protrusion |
| 14 | recess |
| 15 | elongated hole |
| 16 | elevation |
| 17 | spacer wheel |
| 18 | receptacle device |
| 19 | evaluation unit |
| 20 | sensor |
| 21 | fluid-dispensing apparatus |
| 21' | sliding rod |
| 21'' | syringe holder |
| 21''' | fastening mechanism |

The invention claimed is:

1. A device for receiving a syringe in a fluid-dispensing apparatus has
    a) at least two clamps prestressed resiliently, such that the clamps grip the plunger flange of a syringe plunger, and
    b) a housing holding the clamps,
characterized in that
    the clamps independently comprise a holding element, an actuating element, and a cross brace, with at least two protrusions formed on the cross brace, and
    the clamps are independently held in the housing by the cross brace and the at least two protrusions connecting to an elongated hole formed by the housing for each clamp and surrounding the cross brace, at least one elevation formed by the housing for each clamp, and at least one recess formed by the housing for each clamp.

2. The device according to claim 1,
characterized in that
    the holding element and the actuating element of each clamp are designed in one piece.
3. The device according to claim 1,
characterized in that
    a spring mounted in the housing is connected to one of the protrusions of the cross brace and thus prestresses each of the clamps.
4. The device according to claim 1,
characterized in that
    one of the protrusions on the cross brace has a hook shape and another one of the protrusions on the cross brace has a curve shape.
5. The device according to claim 4,
characterized in that
    the hook-shaped protrusion of the cross brace is connected to a pressure plate, and the curve-shaped protrusion of the cross brace is in contact with the at least one recess and the at least one elevation of the housing.
6. The device according to claim 1,
characterized in that
    the housing has a top half and a bottom half.
7. The device according to claim 1,
characterized in that
    the fluid-dispensing apparatus is a dosing pump.
8. The device according to claim 1,
characterized in that
    the fluid-dispensing apparatus is a heparin pump.
9. The device according to claim 1,
characterized in that
    the device is made of a material that has dimensional stability.
10. The device according to claim 9, characterized in that the material is plastic or metal.
11. The device according to claim 1,
characterized in that
    the plunger flange to be gripped varies in thickness from 1.2 mm to 3 mm.
12. The device according to claim 1,
characterized in that
    the at least one elevation has an angle between 0° and 50°.
13. The device according to claim 1,
characterized in that
    the device can be operated with one hand.
14. A medical technical treatment unit containing the device according to claim 1.
15. Use of the device according to claim 1 comprises administering a fluid to a patient.
16. An evaluation unit for the device according to claim 1, has sensors which detect positioning of the plunger flange and of the clamps.
17. The device according to claim 1, characterized in that the fluid-dispensing apparatus is an infusion pump.

* * * * *